United States Patent [19]

Newman et al.

[11] Patent Number: 4,912,059
[45] Date of Patent: Mar. 27, 1990

[54] PHASE SENSITIVE DIFFERENTIAL POLARIMETRY TECHNIQUE AND APPARATUS

[75] Inventors: Arnold L. Newman, Kensington; William D. Stanbro, Columbia, both of Md.

[73] Assignee: The Johns Hopkins University, Baltimore, Md.

[21] Appl. No.: 260,962

[22] Filed: Oct. 21, 1988

[51] Int. Cl.$^4$ .............................................. C12M 1/34
[52] U.S. Cl. ..................................... 435/291; 356/364; 250/225
[58] Field of Search ................ 435/291; 356/364, 365, 356/666; 250/225

[56] References Cited

U.S. PATENT DOCUMENTS 3,856,408 12/1974 Hill et al. ............................ 250/225

FOREIGN PATENT DOCUMENTS 2167447 7/1987 Japan ................................... 435/291

Primary Examiner—Carroll B. Dority, Jr.
Attorney, Agent, or Firm—Robert E. Archibald; Howard W. Califano

[57] ABSTRACT

A differential polarimeter is disclosed for detecting changes in optical rotation between a test cell and reference cell. The test cell contains a fluid sample exposed to an analyte specific enzyme; the reference cell contains a fluid sample not exposed to the enzyme. To enhance the sensitivity of the system a phase sensitive differential polarimetric technique is taught. In this technique, the phase difference between two resulting sinewave voltages is a measure of analyte concentration.

12 Claims, 1 Drawing Sheet

PHASE SENSITIVE DIFFERENTIAL POLARIMETRY TECHNIQUE AND APPARATUS

STATEMENT OF GOVERNMENTAL INTEREST

The Government has rights in this invention pursuant to Contract No. N00039-87-C-5301 awarded by the Department of the Navy.

BACKGROUND OF THE INVENTION

1. Field of the Invention

This invention relates to an improved apparatus for detecting the presence of an analyte in a fluid. In particular, phase sensitive differential polarimetry is used to detect a change in optical rotation caused by an enzyme specific reaction.

2. Description of the Prior or Contemporary Art

It is known in the art that certain enzymes can change the optical rotation of a particular substrate. For instance, when sucrose is heated with the enzyme invertase, it is "inverted" to form one molecule of fructose and one of glucose. Since glucose has a specific rotation of $+66.5°$, fructose has a specific rotation of $-93°$, and glucose $-52.5°$, the total rotation changes from $+66.5°$ to $(-93+52.5)/2 = -20.2°$ upon inversion. By measuring the change in rotation it is possible to determine the presence of an analyte (such as sucrose).

However, the prior art techniques used to measure optical rotation are not adequate for automatic industrial sampling. As described in "Instrumental Methods of Analysis" by Hobart H. Willard et al, 4th ed. (1965) D. Van Nostrand Company, Inc., at pg. 418, the following cumbersome prior art technique is taught: (1) a solution of sucrose (or other analyte) is poured into a test cell; (2) a polarimeter manually operated by the chemist is used to measure the optical rotation of the sample; (3) an enzyme specific to the analyte (i.e., enzyme invertase) is added to the test cell and it is heated; and (4) the test cell is placed in the polarimeter and the change in optical rotation is manually measured. This prior art technique is not suited for on-line automatic analysis of analyte concentration in an industrial process.

SUMMARY OF THE INVENTION

The present invention overcomes the difficulties of the prior art by providing a novel differential polarimetric technique and apparatus. First, differential measuring from two cells is employed. A first cell (or test cell) contains a sample of the fluid that has been exposed to the enzyme. A second cell (or reference cell) contains a sample of the fluid which has not been exposed to the enzyme. First and second beams of polarized light pass through the test and reference cells respectively. A differential analyzing means then compares the relative optical rotation of the first and second beams, and indicates the analyte concentrations.

Second, to enhance sensitivity and to reduce the inaccuracy caused by varying intensities between the two polarized beams, a novel phase sensitive technique is employed. The embodiment of the invention that employs phase sensitive differential polarimetry comprises: an enzyme reactive with the analyte for changing the optical rotation of the analyte; a first beam of polarized light directed through a test cell containing a sample of fluid exposed to the enzyme; a second beam of polarized light directed through a reference cell containing an unexposed sample; a means for providing two essentially synchronized rotating planes of polarization (each beam directed through a different rotating plane); and, first and second electro-optic detectors for detecting the resultant optical beams and for generating two sinusoidal voltages $V_1$ and $V_2$ proportionate to the amplitude of the resulting beams. The phase difference between these two sinewaves is a direct measure of the concentration of the analyte in the test fluid.

The specification teaches several non-limiting techniques for exposing the fluid under test to the enzyme, including: (1) immobilizing the enzyme on a filter matrix placed at the input to the test cell; and (2) immobilizing the enzyme on a surface in the test cell; and (3) periodically injecting enzyme directly into the test cell to mix with the fluid under test. The specification also teaches the use of inlet and outlet ports so that fluid under test can flow into and out of the test and reference cells.

A first novel feature is the use of differential measuring between a reference cell and a test cell. Only in the test cell is the fluid exposed to the enzyme. This feature allows the optical rotation caused by other substances in the fluid to be automatically subtracted. The differential angle of rotation measured between the test and reference cell is a direct measure of the change in optical rotation caused by the enzyme-analyte reaction.

A second novel feature is the use of phase sensitive detection. The light beams emitting from the test and reference cells are passed through rotating polarizers. The resultant optical signals are detected by two electro-optic detectors and two sinusoidal voltages $V_1$ and $V_2$ are generated. If the enzyme has changed the optical rotation of the fluid in the test cell (i.e., by altering the analyte), the phase of the sinewaves $V_1$ will shift with respect to the sinewave $V_2$. This phase difference is detected by and processed by a phase detector circuit.

The above-mentioned features, as well as other features and advantages of the present invention, will become readily apparent from the following non-limiting preferred embodiments and the accompanying drawings.

DETAILED DESCRIPTION OF THE PREFERRED EMBODIMENTS

Optically active substances rotate the plane of polarized light. A molecule of a pure, optically active compound is nonsuperimposable on its mirror image. This property is known as chirality.

The amount of rotation, $\alpha$, depends on sample vessel length, temperature, solvent, concentration (for solutions), pressure (for gases), and light wavelength.

The specific rotation $[\alpha]$ is defined as follows:

$$[\alpha] = \frac{\alpha}{lc} \text{ for solutions}$$

$$[\alpha] = \frac{\alpha}{ld} \text{ for pure compounds.}$$

Where $\alpha$ is the observed rotation, is the cell length in decimeters, c is the concentration in grams per milliliter, and d is the density in the same units. The specific rotation is usually given at a specific temperature and wavelength.

For a mixture of optically active substances, the following approximation applies:

$$\alpha_{total} = \sum_{i=0}^{n} \alpha_i = \frac{1}{l}\left[\frac{\alpha_0}{c_0} + \frac{\alpha_1}{c_1} + \frac{\alpha_2}{c_2} + \ldots + \frac{\alpha_n}{c_n}\right]$$

Thus, the measured optical rotation of a solution of several optically active substances is equal to the sum of the component optical rotations of each chemical species. Using optical rotation measurements for specific chemical analyses presents the problem of separating the analyte's individual component rotation from the total optical rotation of the solution. For example, the optical rotation of a sample of blood plasma is due to several components: glucose, amino acids, proteins, etc. To determine glucose concentration, its individual contribution would have to be separated from the total optical rotation of the plasma sample. This problem is solved in the present invention by differentially sensing the change in optical rotation between a test cell containing a fluid sample exposed to a particular analyte reactive enzyme and a reference cell containing a fluid sample not exposed to the enzyme. When differential measuring is used, the differential angle of rotation measured between the test and reference cells is a direct measure of the change in optical rotation caused by the enzyme analyte-reaction. Optical rotation caused by other substances in the test fluid is automatically subtracted.

Figure 1:
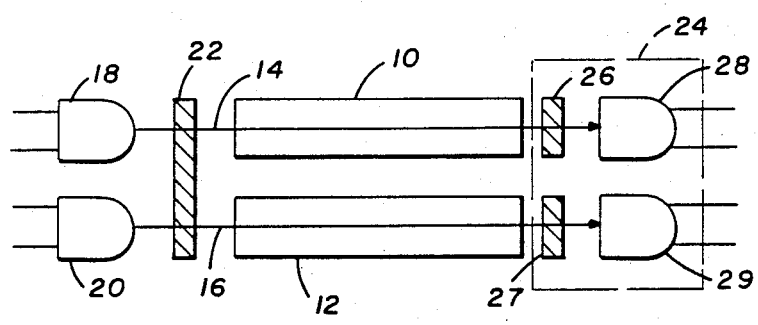
FIG. 1 is a block diagram showing differential polarimetric measuring of a test cell containing a fluid sample exposed to an enzyme and a reference cell containing the fluid sample not exposed to the enzyme.

FIG. 1 is a block diagram of the differential polarimetric measuring apparatus. Test cell 10 contains a sample of the test fluid that has been exposed to a particular enzyme. The enzyme is selected to react with the analyte and alter is chirality, or optical rotation properties. For example, one could detect glucose with the enzyme glucose oxidase. Reference cell 12 contains a sample of the test fluid that has not been exposed to the enzyme. The test and reference cells are generally long thin tubes with optical windows located at each end. A first and second beam of polarized light (14, 16) is directed through the test and reference cells, respectively. The polarized beams can be generated by passing light from two light sources (18, 20), which may be lasers, through a polarizing filter 22. As the polarized beams travel through the cells their angle of rotation will be altered. However, since the fluid in both cells originated from the same sample, any change in optical rotation is attributed solely to a change in rotation in the test cell caused by the enzyme-analyte reaction.

A differential analyzing means 24 compares the relative optical rotation between the first and second polarized beams (14, 16) after they pass through the cells. The difference in angular rotation is proportionate to the concentration of the analyte in the fluid sample. The differential analyzing means 24 may utilize two polarization filters (26, 27) and two electro-optical detectors (28, 29). The polarization filters are generally oriented with the same angle of polarization. If the angle of rotation of the beam passing through the test cell is altered relative to the reference cell, the component of light passing through the polarization filter will change and optical detector 28 will detect a different amplitude. Therefore, the difference in voltage produced by detector 28 and 29 is indicative of the differential optical rotation and in turn a direct measure of analyte concentration.

It is to be understood that other differential analyzing means can be used to measure the relative angle of rotation. For example, an electro-optic modulator could be used, in place of filter 26 and 27, to change the polarization angle until both detectors (28, 29) produce the same voltage output. The applied voltage to the modulator would then be an indication of analyte concentration.

Figure 2:
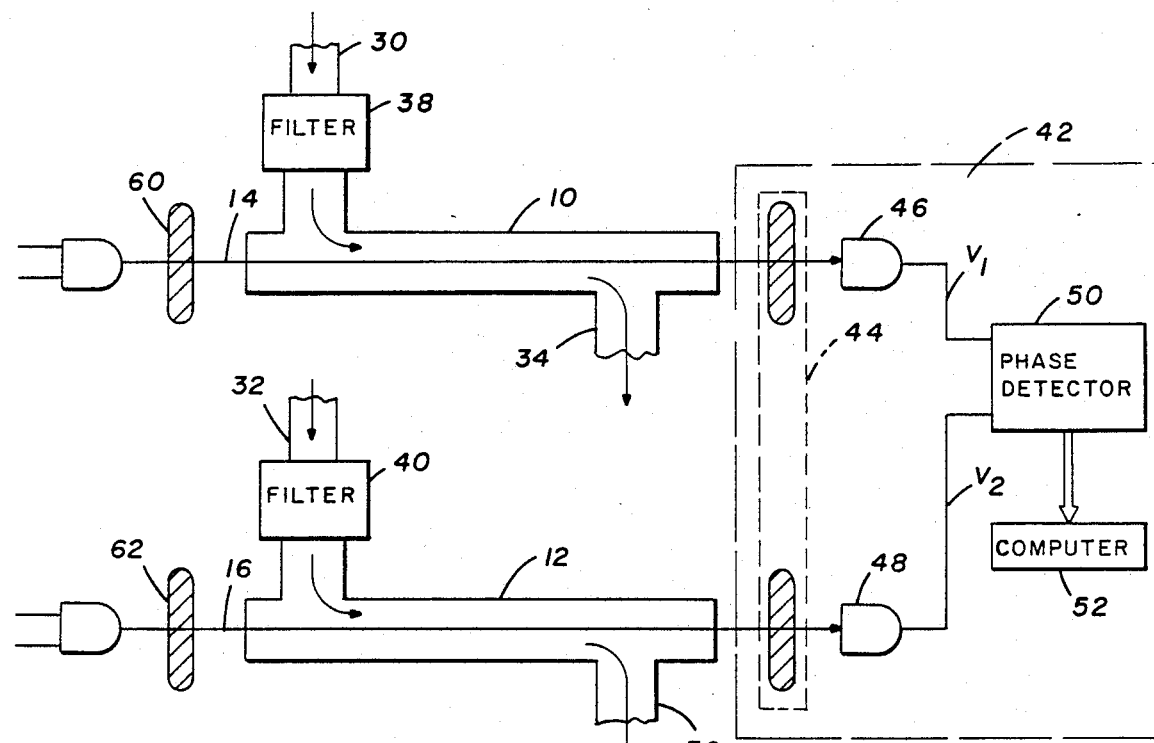
FIG. 2 is a block diagram showing phase sensitive differential polarimetry for detecting a change in optical rotation between the test and reference cells.

FIG. 2 is a block diagram showing a phase sensitive differential polarimeter. Two polarized beams (14, 16) are directed through the test cell 10 and reference cell 12, respectively. Inlet ports (30, 32) and outlet ports (34, 36) allow the fluid sample to flow into and out of the cells. Filters (38, 40) are placed in the inlet port to filter out particulates. In addition, filter 38 may contain the enzyme immobilized on the filter matrix as a means of exposing the fluid to the enzyme as the fluid flows through the filter.

The phase sensitive detector 42 comprises: (1) a rotational means 44 for passing the polarized beams 14, 16 through respective 1st and 2nd essentially synchronous rotating polarization planes; (2) electro-optical detectors 46, 48 for generating sinusoidal waves $V_1$ and $V_2$, dependent on the component of the optical beam passed by the rotational means; and, (3) a phase detector means 50 for comparing the phase of sinusoidal voltages $V_1$ and $V_2$. The phase difference between $V_1$ and $V_2$ is indicative of analyte concentrations. A computer 52 can be used to calculate the actual analyte concentration, taking into account temperature, flow rate and other measurable variables.

Figure 4:
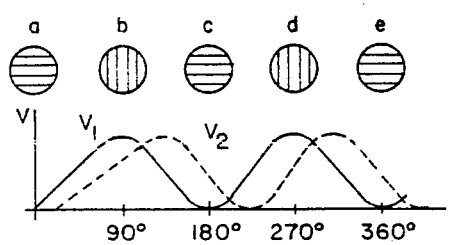
FIG. 4 is a plot of the resulting sinusoidal voltage generated at the output of the polarimetric analyzing means.
Figure 3:
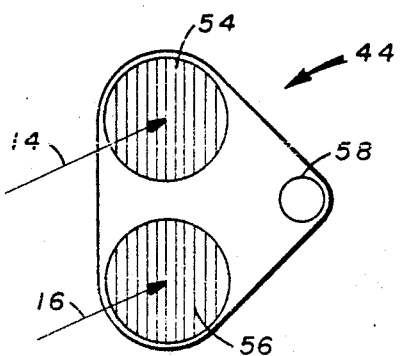
FIG. 3 is a diagram of the polarimetric analyzing means for rotating two polarization planes synchronously through 360°.

FIG. 3 is a diagram of the rotational means 44. First and second polarizers 54, 56 are rotated in an essentially synchronous manner by motor drive 58. The first and second beam 14, 16 (after passing through the test and sample cells respectively) pass through the 1st and 2nd rotating polarizers 54, 56. FIG. 4 is a plot of the resultant sinusoidal voltage generated by the detectors. The plane of polarization generated by rotating polarizers is shown as a-e, that is: (a) shows a 0° rotation; (b) 90° rotation; (c) 180° rotation; (d) 270° rotation; and (e) 360° rotation. As the polarized optical beams 14, 16 pass through the cells their rotation angle will changed. As the resulting beam passes through their respective polarizers 54, 56 and are detected by electro-optical detectors (46, 48), sinusoidal voltages $V_1$ and $V_2$ are produced. If analyte is present in the test cell, the phase of the sinewave $V_1$ will shift with respect to the reference sinewave $V_2$, as shown in FIG. 4. This phase shift is directly related to the difference in optical rotation between the test and reference cells caused by the analyte-enzyme reaction, and therefore is directly indicative of the analyte concentration.

It will be understood that other techniques for generating the sinewave voltage are contemplated and within the scope of the present invention. For example, the polarizers 54, 56 could have a fixed angle of rotation and the initial beams can be rotated. That is polarizing filters 60 and 62 could be rotated, as generally taught by FIG. 3, and the angle of polarization of beam 14 and 16 would be rotating in synchronization.

It is also to be understood that there are various ways to bring the analyte in contact with the enzyme. As discussed, the enzyme could be immobilized on the filter matrix 38. The enzyme could be immobilized on the wall or other surface within the test cell. Alternatively, the enzyme could be directly injected into the sample fluid and into the test cell. In this instance the enzyme itself would alter the optical rotation since it is in solution. However, the presence of the enzyme in solution could be electronically subtracted or compensated for.

Obviously, many modifications and variations of the present invention are possible in light of the above teachings. It is, therefore, to be understood that within the scope of the appended claims, the invention may be practiced otherwise than is specifically described.

What is claimed is:

1. A device for detecting the presence of an analyte in a fluid comprising:
   an enzyme adapted to react with the analyte changing the optical rotation of the analyte;
   means forming a first beam of polarized light directed to a test cell containing a sample of the fluid that has been exposed to said enzyme;
   means forming a second beam of polarized light directed through a reference cell containing a sample of the fluid which has not been exposed to said enzyme; and,
   a differential analyzing means for comparing the relative optical rotation of said first and second beams after they pass through said test and reference cells respectively, thereby indicating the concentration of the analyte in the fluid.

2. The device of claim 1, wherein said test and reference cells each have an inlet and outlet, so that a sample of the fluid can flow into and out of each cell.

3. The device of claim 2, further comprising a filter placed at the inlet to said test cell to remove particulates.

4. The device of claim 2, further comprising a filter placed at the inlet to said test cell, said enzyme being immobilized on said filter.

5. The device of claim 1, wherein said enzyme is immobilized on a surface in said test cell.

6. The device of claim 1, wherein said differential analyzing means further comprises:
   a first polarizer and a first detector means for generating an electrical signal proportional to the first beam after passing through said test cell; and,
   a second polarizer and a second detector means for generating an electrical signal proportional to the second beam after passing through said test cell.

7. The device of claim 6, further comprising:
   a means for rotating the plane of polarization in said first and second polarizer in an essentially synchronous manner; and,
   a phase detector electrically coupled to said first and second detector means for detecting the phase shift between the electrical signals generated by said first and second detector means, wherein the phase shift is indicative of the concentration of analyte in the fluid.

8. The device of claim 1, further comprising:
   a rotation means for rotating the plane of polarization of said first and second beam of polarized light, prior to those beams entering the test and reference cell, respectively, in an essentially synchronize manner; and wherein said differential analyzing means includes a means to analyze the phase difference between said first and second beams after they pass through said test and reference cells.

9. A device for detecting the presence of an analyte in a fluid comprising:
   an enzyme adapted to react with the analyte changing the optical rotation of the analyte;
   means forming a first beam of polarized light directed through a test cell containing a sample of the fluid that has been exposed to said enzyme;
   means forming a second beam of polarized light directed through a reference cell containing a sample of the fluid that has not been exposed to said enzyme;
   a rotational means for passing the first and second beams through respective first and second essentially synchronous rotating polarization planes;
   a first detection means for detecting the amplitude of the first beam that passes through the rotational means, thereby providing a sinusoidal voltage $V_1$;
   a second detection means for detecting the amplitude of the 2nd beam that passes through the rotational means, that produces a sinusoidal voltage $V_2$;
   a phase detector means for detecting the phase difference between sinusoidal voltage $V_1$ and $V_2$, the phase difference is indicative of analyte concentration.

10. The apparatus of claim 9, wherein said test and reference cells each have inlet and outlet, so that a sample of the fluid can flow into and out of each cell.

11. The device of claim 10, wherein said rotational means further comprises:
    a first polarizer optically coupled to the first beam after it passes through said test cell;
    a second polarizer optically coupled to said second beam after it passes through said reference cell; and,
    a means for rotating said first and second polarizers in an essentially synchronous manner.

12. A device for detecting the presence of an analyte in the fluid comprising:
    an enzyme adapted to react with the analyte changing the optically rotation of the analyte;
    a test cell containing a sample of the fluid which is exposed to said enzyme;
    a reference cell containing a sample of the fluid which has not been exposed to said enzyme;
    a means for generating a first and second beam of polarized light adapted to pass through said first and second cell, respectively, wherein said first and second beam of polarized light each have a plane of polarization that is rotated in an essentially synchronize manner; and,
    a differential analyzing means optically coupled to the first and second beams after they pass through said test and reference cells, respectively, for comparing the relative phase shift between said first and second beams, thereby indicating the concentration of analyte in the fluid.

* * * * *